United States Patent [19]

Shaber et al.

[11] Patent Number: 5,527,816

[45] Date of Patent: Jun. 18, 1996

[54] FUNGICIDAL 2-ARYL-2-CYANO-2-(ARYLOXYALKYL) ETHYL-1,2,4-TRIAZOLES

[75] Inventors: Steven H. Shaber, Horsham, Pa.; Ted T. Fujimoto, Churchville, Pa.

[73] Assignee: Rohm and Haas Company, Philadelphia, Pa.

[21] Appl. No.: 392,282

[22] Filed: Feb. 22, 1995

Related U.S. Application Data

[63] Continuation of Ser. No. 749,841, Aug. 26, 1991, abandoned.

[51] Int. Cl.[6] .......................... A01N 43/64; C07D 249/08
[52] U.S. Cl. ........................ 514/383; 548/267.4
[58] Field of Search .................... 548/267.4; 514/383

[56] References Cited

U.S. PATENT DOCUMENTS 4,366,165  12/1982  Miller et al. .................... 514/383
4,507,140  3/1985  Sugavanam ....................... 71/76
4,663,463  5/1989  Kunz et al. ...................... 548/262

*Primary Examiner*—Floyd D. Higel
*Attorney, Agent, or Firm*—Joseph F. Leightner

[57] ABSTRACT

2-aryl-2-cyano-2-(aryloxyalkyl)ethyl-1,2,4-triazoles of the formula

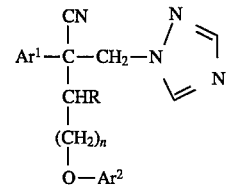

wherein $Ar^1$ and $Ar^2$ are optionally substituted aryl groups which may or may not be different, R is hydrogen or alkyl, n is an integer of at least one, and the agronomically acceptable enantiomorphs, acid addition salts and metal salt complexes thereof, compositions containing these compounds and their uses as fungicides, particularly against phytopathogenic fungi.

14 Claims, No Drawings

FUNGICIDAL 2-ARYL-2-CYANO-2-(ARYLOXYALKYL) ETHYL-1,2,4-TRIAZOLES

This application is a continuation of application Ser. No. 07/749,841, filed Aug. 26, 1991, now abandoned.

FIELD OF THE INVENTION

This invention relates to 2-aryl-2-cyano-2-(aryloxyalkyl)ethyl-1,2,4-triazoles, their enantiomorphs, acid addition salts and metal complexes, compositions containing these compounds, and the use of these compounds as fungicides.

BACKGROUND OF THE INVENTION

Substituted alkyl triazoles are known to be useful as fungicides. For example, Miller, et al., U.S. Pat. No. 4,366,165 disclose 1- and 4-arylcyanoalkyl-1,2,4-triazoles as fungicidal agents. No aryloxyalkyl substituents are disclosed. Sugavanam, U.S. Pat. No. 4,507,140, discloses as fungicides a broad class of di- and tri-substituted butenyl, butynyl or butyl imidazoles and triazoles. However, none of this art suggest the specific class of triazoles of the present invention.

DESCRIPTION OF THE INVENTION

This invention relates to 2-aryl-2-cyano-2-(aryloxyalkyl) ethyl-1,2,4-triazoles of the formula

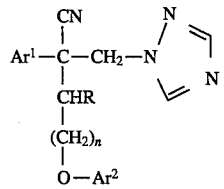

wherein
- $Ar^1$ and $Ar^2$ are each optionally substituted aryl groups which may or may not be different,
- n is an integer of at least one,
- R is hydrogen or alkyl, and
- the agronomically acceptable enantiomorphs, acid addition salts and metal salt complexes thereof, compositions containing these compounds and their uses as fungicides, particularly against phytopathogenic fungi.

This invention relates to compounds of the general formula (I) wherein
- $Ar^1$ and $Ar^2$ are each independently ($C_6$–$C_{10}$)aryl groups optionally substituted with one, two or three substituents each independently selected from the group consisting of halogen, ($C_1$–$C_4$)alkyl, halo($C_1$–$C_4$)alkyl, ($C_1$–$C_4$)alkoxy, halo($C_1$–$C_4$)alkoxy, ($C_1$–$C_4$)alkylthio, cyano, hydroxy, nitro, dialkylamino, N-alkyl-N-(alkylcarbonyl)amino, phenoxy, phenoxy mono-substituted with halogen, ($C_1$–$C_4$)alkyl, ($C_1$–$C_4$)alkoxy or trifluoromethyl, phenyl and phenyl mono-substituted with halogen, ($C_1$–$C_4$)alkyl, ($C_1$–$C_4$)alkoxy or trifluoromethyl;
- R is hydrogen or ($C_1$–$C_4$)alkyl;
- n is an integer from one to about twelve; and
- the agronomically acceptable enantiomorphs, acid addition salts and metal salt complexes thereof.

A preferred embodiment of this invention is the compounds, enantiomorphs, salts and complexes of Formula (I) wherein
- $Ar^1$ and $Ar^2$ are each independently naphthyl, preferably phenyl, optionally substituted with one or two substituents each independently selected from the group consisting of halogen, ($C_1$–$C_4$)alkyl, halo($C_1$–$C_4$)alkyl, ($C_1$–$C_2$)alkoxy, halo($C_1$–$C_2$)alkoxy, and N-alkyl-N-(alkylcarbonyl)amino,
- R is hydrogen or methyl, and
- n is an integer from one to about four.

A more preferred embodiment of this invention is the compounds, enantiomorphs, salts and complexes of Formula (I) wherein
- $Ar^1$ and $Ar^2$ are each independently phenyl or phenyl substituted with one or two substituents each independently selected from the group consisting of halogen, ($C_1$–$C_2$)alkyl, halo($C_1$–$C_2$)alkyl, ($C_1$–$C_2$)alkoxy, halo($C_1$–$C_2$)alkoxy and N-acetyl-N-methylamino, and
- R is hydrogen.

An even more preferred embodiment of this invention is the compounds, enantiomorphs, salts and complexes of Formula (I) wherein $Ar^1$ and $Ar^2$ are each independently selected from the group consisting of phenyl, phenyl substituted with one or two halogens selected from fluoro, chloro and bromo, and 4-(N-acetyl-N-methylamino)phenyl.

A most preferred embodiment of this invention is the compounds, enantiomorphs, salts and complexes of Formula (I) wherein $Ar^1$ is phenyl, 4-chlorophenyl, 4-fluorophenyl, 2,4-dichlorophenyl or 2,4-difluorophenyl and $Ar^2$ is phenyl, 4-chlorophenyl, 4-fluorophenyl, 2,4-dichlorophenyl, 2,4-difluorophenyl, 4-bromophenyl or 4-(N-acetyl-N-methylamino)phenyl.

The terms "$Ar^1$" and "$Ar^2$" (aryl) as used in the present specification mean an aromatic ring structure of six to ten carbon atoms, preferably a phenyl or naphthyl group.

Typical aryl groups encompassed by this invention are phenyl, naphthyl, 4-chlorophenyl, 2,4-dichlorophenyl, 2,4,6-trichlorophenyl, 4-fluorophenyl, 2,4-difluorophenyl, 4-bromophenyl, 2,4-dibromophenyl, 4-iodophenyl, 2,4-dimethylphenyl, 4-ethylphenyl, 4-fluoro-2-methylphenyl, 2-chloro-4-methylphenyl, 2,4-dinitrophenyl, 4-methylphenyl, 3-isobutylphenyl, 2-methoxyphenyl, 4-(2-chloroethyl)phenyl, 4-(t-butoxy)phenyl, 2-(difluoromethoxy)phenyl, 4-(trifluoromethoxy)phenyl, 4-(methylthio)phenyl, 4-hydroxyphenyl, 4-phenoxyphenyl, 4-(2'-methylphenoxy)phenyl, 4-(trichloromethyl)phenyl, 2-nitrophenyl, 2,4-dicyanophenyl, 4-(2'-methoxyphenoxy)phenyl, 4-(4'-chlorophenyl)phenyl, 2-(methylthio)phenyl, 4-(chloromethyl)phenyl, 2-(fluoromethyl)phenyl, 4-cyanophenyl, 3-hydroxyphenyl, 4-(trifluoromethyl)phenyl, 4-phenylphenyl, 4-(4'-chlorophenyl)phenyl, 2-chloro-4-(4'-chlorophenoxy)phenyl and 4-(N-acetyl-N-methylamino)phenyl.

Alkyl includes straight and branched alkyl groups, for example ($C_1$–$C_4$)alkyl such as methyl, ethyl, n-propyl, isopropyl, n-butyl, isobutyl, sec-butyl or t-butyl.

Alkoxy is, for example, ($C_1$–$C_4$)alkoxy such as methoxy, ethoxy and t-butoxy.

Alkylthio is, for example, ($C_1$–$C_4$)alkylthio such as methylthio, ethylthio and isopropylthio.

Dialkylamino is, for example, dimethylamino or N-methyl-N-ethylamino.

N-alkyl-N-(alkylcarbonyl)amino is, for example, N-acetyl-N-methylamino or N-(ethylcarbonyl)-N-methylamino.

Halo is fluoro, chloro, bromo and iodo.

Haloalkyl is, for example, halo($C_1$–$C_4$)alkyl such as chloromethyl, fluoromethyl, difluoromethyl, 1-chloroethyl, 1,1-difluoroethyl, trifluoromethyl, 3-chloropropyl, 1-bromo-2-methylpropyl and 2,3-dichloropropyl.

Haloalkoxy is, for example, halo($C_1$–$C_4$)alkoxy such as difluoromethoxy, chloromethoxy, 2-bromoethoxy, 1,1-difluoroethoxy, 1,1-dibromopropoxy and 1-chloro-2-methyl-2-propoxy.

This invention also includes the acid addition salts of the compounds of formula (I) wherein the anionic counterion of an acid is selected in such a manner that the sum of the valence charges of the protonated triazole compound and the anion equals zero.

This invention further includes the metal salt complexes of the compounds of formula (I) wherein the metal is a cation selected from Groups IIA, IVA, IB, IIB, VIB, VIIB and VIII of the Periodic Table and the anionic counterion is selected in such a manner that the sum of the valence charges of the cation and anion equals zero.

The 2-aryl-2-cyano-2-(aryloxyalkyl)ethyl-1,2,4-triazoles of this invention can be prepared by conventional synthetic routes. For example, they may be prepared as shown by Scheme A:

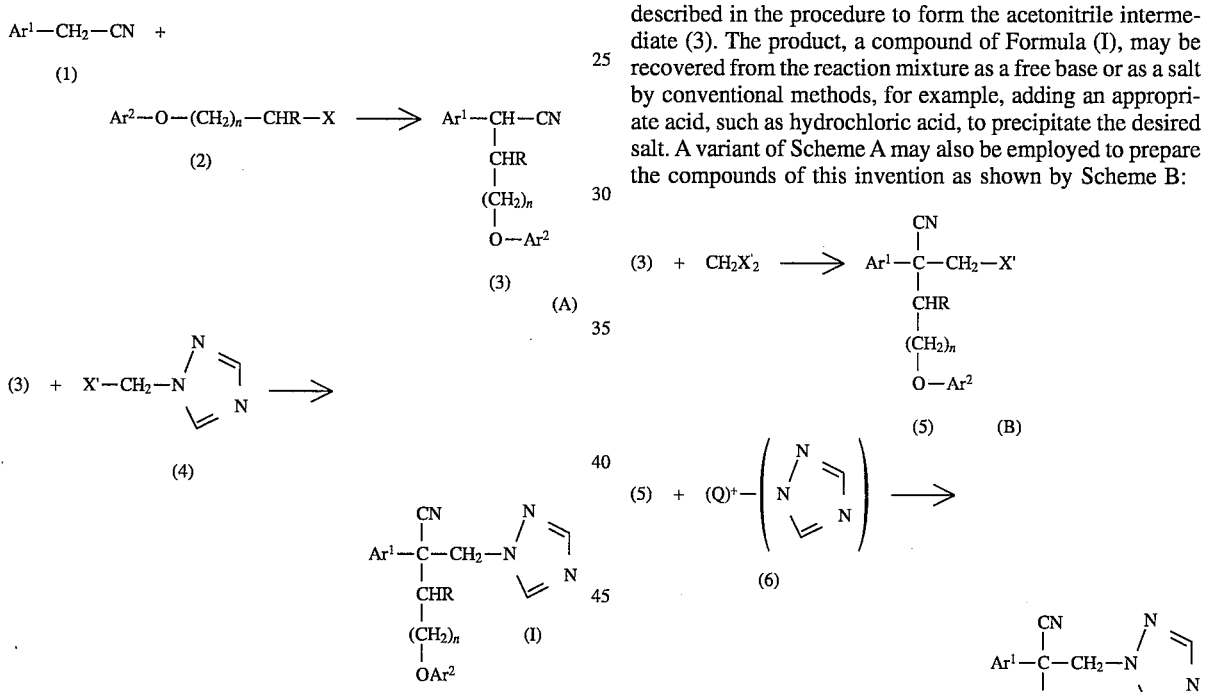

wherein $Ar^1$, $Ar^2$, R and n are as described for Formula (I), X is a chloride, bromide, iodide, methylsulfonate, phenylsulfonate, 4-tolylsulfonate or any other leaving group capable of effecting the desired reaction, and X' is a chloride or bromide. Processes for the alkylation of nitrile stabilized carbanions are disclosed in the literature, for example, S. Arseniyadis, K. S. Kyler and D. S. Watt in *Organic Reactions*, 31, pages 1–72 (general review) and pages 73–343 (specific examples), the disclosure of which is incorporated by reference herein.

Appropriately substituted arylmethyl cyanides (1) are reacted with the aryloxyalkyl chloride, bromide, iodide, methylsulfonate, phenylsulfonate or 4-tolylsulfonate (2) under basic conditions at a temperature from about −20° C. to about 100° C., preferably from about −10° C. to about 60° C. Examples of suitable bases include a Group IA metal, preferably sodium or potassium, hydroxide, hydride, t-butoxide, methoxide, and dimsylate. Hydride, t-butoxide and dimsylate bases are used in solvents such as toluene, dimethyl sulfoxide (DMSO), N,N-dimethylformamide (DMF), glyme, ether and (THF). An alternative procedure to prepare the acetonitrile intermediate (3) employs phase transfer conditions in the presence of a base, such as hydroxide, with solvents such as methylene chloride, chloroform, carbon tetrachloride, benzene, toluene, ethers, tetrahydrofuran (THF) and dioxane. The phase transfer conditions usually require catalysts, examples of which include tetrabutylammonium hydroxide, tetrabutylammonium bromide, benzyltriethylammonium chloride or other quaternary ammonium salts, quaternary phosphonium salts and crown ethers, for example, 18-crown-6. The resulting 2-aryl-2-(aryloxyalkyl)acetonitrile (3) is preferably purified, for example, by distillation, and then reacted with about 1.1 equivalents of a base as described above at a temperature of from about 0° C. to about 50° C. with a 1-halomethyl-1,2,4-triazole (4), for example, 1-bromomethyl-1,2,4-triazole or, using about 2.2 equivalents of a base, with a salt, for example, the hydrochloride salt, of a 1-halomethyl-1,2,4-triazole (4), for example, 1-chloromethyl-1,2,4-triazole. The 1-halomethyl-1,2,4-triazole or a salt thereof may be added as a solid or a solution using as a solvent one of or a mixture of the solvents described in the procedure to form the acetonitrile intermediate (3). The product, a compound of Formula (I), may be recovered from the reaction mixture as a free base or as a salt by conventional methods, for example, adding an appropriate acid, such as hydrochloric acid, to precipitate the desired salt. A variant of Scheme A may also be employed to prepare the compounds of this invention as shown by Scheme B:

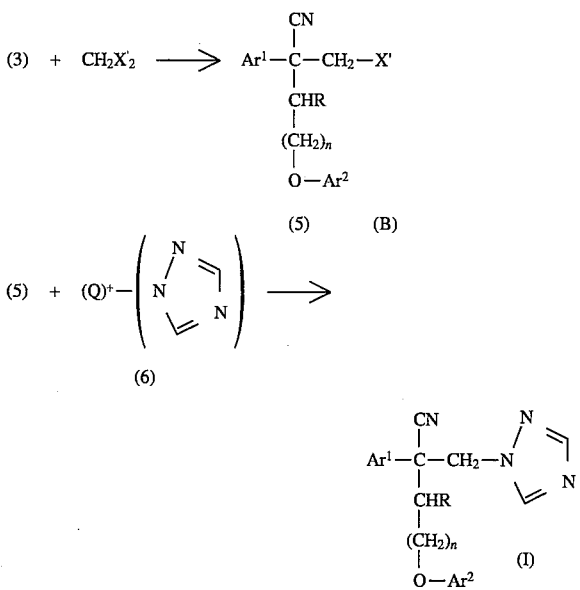

wherein $Ar^1$, $Ar^2$, R, n, and X' are as described in Scheme A and $(Q)^+$ is the cation of an alkali metal, preferably sodium or potassium. The compound (5) is prepared by chloro- or bromomethylation of compound (3) by methylene chloride or methylene bromide, using from about one to about two equivalents of the methylene halide to the acetonitrile intermediate (3), under basic conditions at a temperature from about 0° C. to about 150° C., preferably from about 25° C. to about 60° C. Examples of suitable bases include a Group IA metal, preferably sodium or potassium, hydroxide, hydride, t-butoxide, and methoxide. Alternatively, phase transfer conditions can be used to prepare Intermediate (5) as described for Intermediate (3) in Scheme (A). The triazoles of this invention are then prepared by nucleophilic displacement of the chloro or bromo atom of compound (5) by a salt, preferably a Group IA metal salt such as potassium or sodium, of the triazole (6) using from about one to about three equivalents of the triazole salt for each equivalent of intermediate (5). This reaction can be run either neat or, preferably, in an appropriate solvent such as DMSO, DMF, toluene or xylene at a temperature of from about 0° C. to about 150° C., preferably from about 50° C. to about 130° C. The substituted aryloxyalkyl compounds (2) used in both Schemes A and B may be conveniently synthesized, if necessary, from commercially available materials using Scheme C:

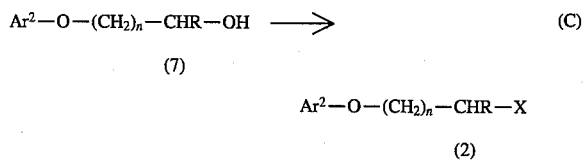

wherein $Ar^2$, R, n, and X are as defined in Scheme A. The alcohol (7) may be reacted with a sulfonyl chloride, for example, methylsulfonyl chloride, in the presence of an acid acceptor, for example, triethylamine (TEA), either neat or in the presence of a suitable solvent, for example, THF, to form the aryloxyalkyl methylsulfonate. Alternatively, the alcohol (7) may be reacted with a suitable halogenating agent, for example, thionyl chloride, triphenylphosphine plus carbon tetrachloride, and N-bromosuccinimide plus triphenylphosphine, either neat or in the presence of a suitable solvent, for example, chloroform.

An alternative synthesis of aryloxyalkyl compounds (2) is the reaction of an aryloxide salt (8) with an alkylene dihalo compound (9) using Scheme D:

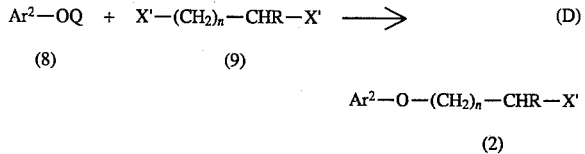

wherein $Ar^2$, R, n, and X' are as defined in Scheme A and Q is a Group IA metal such as sodium or potassium. The optionally substituted aryloxide salt (8) can be conveniently formed from the corresponding optionally substituted hydroxyaryl compound by reaction with a base, for example, potassium or sodium hydroxide. The aryloxide salt (8) is then alkylated with an alkylene dihalo compound (9), for example, methylene dibromide, ethylene dichloride or 1,3-dibromopropane, in the presence of a polar solvent, for example, DMSO, DMF or an alcohol such as methanol or ethanol to form compound (2). The aryloxide salt (8) may also be formed in situ by reaction with a base such as potassium t-butoxide if desired.

The alkyl portion of the aryloxyalkyl compound (2) can be readily homologated using known techniques, for example, as described in Scheme E:

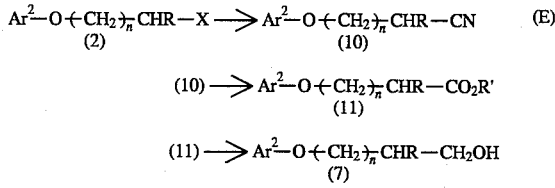

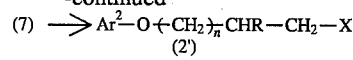

wherein $Ar^2$, n and X are defined in Scheme (A), R is hydrogen and R' is either hydrogen or alkyl, for example, methyl, ethyl, propyl, and butyl. The aryloxyalkyl chloride, bromide, methylsulfonate, phenylsulfonate or 4-tolylsulfonate (2) is reacted with a cyanide, for example, potassium or sodium, to provide the nitrile of formula (10). The nitrile is hydrolyzed with aqueous acid, for example, sulfuric acid, or aqueous base, for example, sodium hydroxide, to yield the carboxylic acid of formula (11) or the nitrile is reacted with a dry acid, for example, anhydrous hydrochloric acid, in the presence of an alcohol, for example, methyl or n-butyl alcohol, to yield a carboxylic ester of formula (11). The aryloxyalkyl carboxylic acid or ester of formula (11) is reduced with, for example, lithium aluminum hydride or diborane, in a solvent such as dimethyl ether, THF, or dioxane to obtain its corresponding alcohol of formula (7). The alcohol of formula (7) is converted to a aryloxyalkyl chloride, bromide, methylsulfonate, phenylsulfonate, or 4-tolylsulfonate (2') by methods identical to those described in Scheme C.

The acid addition salts of the 1,2,4-triazoles of this invention can be prepared by techniques which are well known in the art. A 1,2,4-triazole of Formula (I) can be dissolved in an appropriate polar solvent, for example, diethyl ether, THF, ethanol, methanol or combinations thereof, and reacted at a temperature from about 0° C. to about 50° C. with an equivalent or excess amount of a mineral or organic acid, for example, hydrochloric, sulfuric, nitric, phosphoric, and acetic which may or may not be dissolved in a solvent common to the solvent of the triazole solution. The mixture is then either cooled or evaporated to give an acid addition salt of the compounds of Formula (I) which can be either used as such or recrystallized from an appropriate solvent or combination of appropriate solvents, for example, methanol, chloroform, acetone, diethyl ether, and THF.

The metal salt complexes of the 1,2,4-triazoles of this invention can be prepared by adding dropwise, with stirring, a stoichiometric amount of a metal salt, for example, zinc (II) chloride and copper (II) chloride, dissolved in an appropriate solvent or combination of solvents to a solution of the 1,2,4-triazole. The reaction mixture is briefly stirred and the solvent is removed, for example, by distillation, to give a metal salt complex of the compounds of Formula (I).

An alternative preparation of these metal salt complexes involves mixing stoichiometric or excess amounts of the metal salt and a triazole of Formula (I) in a solvent containing adjuvants just prior to spraying the plants. Adjuvants that may be included in this in-situ formulation preparation are detergents, emulsifiers, wetting agents, spreading agents, dispersing agents, stickers, and adhesives which are used in agricultural applications.

Solvents that can be utilized in both of these procedures to prepare metal salt complexes include any polar solvent, for example, water, methanol, ethanol, isopropanol or ethylene glycol and any aprotic dipolar solvent, for example, DMSO, acetonitrile, DMF, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, and barium.

Examples of anions that can be used as the counterion in the metal salt include, but are not limited to, chloride, bromide, iodide, sulfate, bisulfate, phosphate, nitrate, perchlorate, carbonate, bicarbonate, hydrosulfide, hydroxide, acetate, oxalate, malate, and citrate.

Metal containing fungicides can also act as a safening agent when used in place of metal salts. Typical metal containing fungicides that can be utilized with the triazoles of this invention are: (1) dithiocarbamates and derivatives such as ferbam, ziram, maneb and its zinc ion coordination product mancozeb, and zineb; (2) copper based fungicides such as cuprous oxide, copper oxychloride, copper naphthenate and Bordeaux mixture; and (3) miscellaneous fungicides such as phenylmercuric acetate, N-ethylmercuri-1,2,3,6-tetrahydro-3,6-endomethano- 3,4,5,6,7,7-hexachlorophthalimide, phenylmercuri monoethanolammonium lactate, nickel containing compounds and calcium cyanamide.

The compounds of this invention possess an asymmetric carbon atom and thus exist as racemic mixtures. The D and L enantiomorphs in these racemic mixtures can be separated via standard techniques such as fractional crystallization using, for example, D-tartaric acid, L-tartaric acid, and L-quinic acid followed by basification and extraction of the D or L enantiomorph free base.

The following examples in Table 1 are provided to illustrate the present invention. Melting points are provided in the experimental section for those examples which are solids and NMR data are provided in Table 2 for examples whose physical state is a non-solid.

TABLE 1

$$Ar^1-\underset{\underset{O-Ar^2}{\overset{|}{(CH_2)_n}}}{\overset{\overset{CN}{|}}{C}}-CH_2-N\underset{\diagdown}{\overset{\diagup}{N}}\underset{N}{\diagdown}$$

| Ex. No. | Ar$^1$ | n | Ar$^2$ |
|---|---|---|---|
| 1 | 4-chlorophenyl | 2 | phenyl |
| 2 | phenyl | 2 | phenyl |
| 3 | phenyl | 3 | phenyl |
| 4 | phenyl | 4 | phenyl |
| 5 | phenyl | 2 | 4-bromophenyl |
| 6 | phenyl | 2 | 4-chlorophenyl |
| 7 | 4-chlorophenyl | 3 | 4-(N-acetyl-N-methylamino)phenyl |

TABLE 2

NMR Data

| Ex. No. | 60 MHz, Delta Scale in ppm, Tetramethylsilane (TMS) Standard, CDCl$_3$ Solvent |
|---|---|
| 1 | 2.4–2.8(m, 1H), 3.8–4.2(m, 2H), 4.4–5.0(q, 2H), 6.6–7.4(m, 10H), 7.9(s, 1H), 8.0(s, 1H) |
| 5 | 2.5–2.7(t, 2H), 3.9–4.1(m, 2H), 4.6–4.9(q, 2H), 6.7–7.4(m, 9H), 7.9(s, 2H) |
| 6 | 2.4–2.8(m, 2H), 3.8–4.1(m, 2H), 4.6–4.7(q, 2H), 6.6–7.4(m, 9H), 7.9(s, 1H), 8.0(s, 1H) |
| 7 | 1.2–1.6(m, 4H), 1.8(s, 3H), 2.0–2.6(m, 2H), 3.2(s, 3H), 4.6–4.9(q, 2H), 6.7–7.4(m, 8H), 7.9(s, 1H), 8.0(s, 1H) |

EXAMPLE 1

Preparation of 1-[2-(4-Chlorophenyl)-2-cyano-4-phenoxybutyl]-1,2,4-triazole a. Preparation of 1-Chloro-2-phenoxyethane To a flask was added 41.5 grams (g.) (0.3 mole) of 2-phenoxyethanol, 50 ml of toluene and 3.93 g. of pyridine, then 39.3 g. (0.33 mole) of thionyl chloride dropwise while stirring at room temperature. The exothermic reaction was heated at 50°–60° C. for two hours. After cooling to room temperature, the resulting salt was filtered and washed with methylene chloride. The filtrate was washed several times with aqueous sodium bicarbonate, dried using sodium sulfate, and then concentrated to obtain 39 g. of the 1-chloro-2-phenoxyethane as a yellow oil (83% yield).

b. Preparation of 2-(4-Chlorophenyl)-4-phenoxybutanenitrile

To a flask was added 7.2 g. (0.150 mole) of a 50% oil dispersion of sodium hydride. After washing the sodium hydride several times with hexane to remove the mineral oil, 18.9 g. (0.125 mole) of 4-chlorobenzyl cyanide in 50 ml of dry DMF was added dropwise at 0° C. Upon completion of the addition, the reaction was stirred for one hour while warming to room temperature, then 20.0 g. (0.128 mole) of 1-chloro-2-phenoxyethane was added dropwise at 15° C. over a 30 minute period. The stirred reaction was allowed to warm to room temperature and was complete in two hours. The reaction mixture was diluted with 300 ml. of water and extracted three times with 100 ml. portions of methylene chloride. The combined extracts were washed with dilute hydrochloric acid and water followed by drying using sodium sulfate. Upon removal of the solvent, 33 g. of the crude 2-(4-chlorophenyl)-4-phenoxybutanenitrile was obtained (96% yield).

c. Preparation of 1-Bromo-2-(4-chlorophenyl)-2-cyano-4-phenoxybutane

To a flask was added 6.1 g. (0.127 mole) of a 50% oil dispersion of sodium hydride. After washing the sodium hydride several times with hexane to remove the mineral oil, 50 ml. of dry DMF was added, then a solution of 30 g. (0.11 mole) of 2-(4-chlorophenyl)-4-phenoxybutanenitrile in 25 ml. of dry DMF was added dropwise at 0° C. The reaction was stirred and allowed to warm to room temperature over 1.5 hours, then 21.2 g. (0.127 mole) of dibromomethane was added dropwise at 15° C. Upon completion of the addition, the reaction was stirred and heated to 50° C. and was complete in three hours. The reaction mixture was cooled to room temperature, diluted with 300 ml. of water, and then extracted three times with 100 ml. portions of methylene chloride. The combined extracts were washed with dilute hydrochloric acid and water, then dried using sodium sulfate. Upon removal of the solvent, 31 g. of 1-bromo-2-(4-chlorophenyl)-2-cyano-4-phenoxybutane was obtained (77% yield).

d. Preparation of 1-[2-(4-Chlorophenyl)-2-cyano-4-phenoxybutyl]- 1,2,4-triazole

To a flask was added 10.0 g. (0.0935 mole) of potassium triazole in 75 ml. of DMSO. The mixture was stirred and heated at 50° C., then 31.0 g. (0.085 mole) of 1-bromo-2-(4-chlorophenyl)-2-cyano-4-phenoxybutane in 25 ml. of DMSO was added dropwise. The reaction was stirred for 18 hours at 100° C., then cooled to room temperature, diluted with 300 ml. of water, and extracted three times with 100 ml. portions of methylene chloride. The combined extracts were washed with water, dried using sodium sulfate, and concentrated to obtain 27 g. of a dark brown oil that was purified using column chromatography. The impurities were eluted with 500 ml. of a 9 to 1 mixture of hexane and ethyl acetate and 500 ml. of a 3 to 1 mixture of hexane and ethyl acetate. The compound was eluted with a 1 to 1 mixture of hexane and ethyl acetate, then 800 ml. of ethyl acetate to obtain 11.5 g. (37% yield) of the product as a thick oil.

EXAMPLE 2

Preparation of
1-(2-Cyano-2-phenyl-4-phenoxybutyl)-1,2,4-triazole

This compound (3.5 g.) was prepared using the procedures described in Examples 1a, b, c, and d except using benzyl cyanide in Example 1b and was obtained as a white solid whose melting point was 64°–66° C.

EXAMPLE 3

Preparation of
1-(2-Cyano-2-phenyl-5-phenoxypentyl)-1,2,4-triazole

This compound (4.0 g.) was prepared using the procedures described in Examples 1b, c, and d except using benzyl cyanide and 1-bromo-3-phenoxypropane in Example 1b and was obtained as a white solid whose melting point was 85°–86° C.

EXAMPLE 4

Preparation of
1-(2-Cyano-2-phenyl-6-phenoxyhexyl)-1,2,4-triazole

This compound (12.8 g.) was prepared using the procedures described in Examples 1b, c, and d except using benzyl cyanide and 1-bromo-4-phenoxybutane in Example 1b, and was obtained as a solid whose melting point was 95°–96° C.

EXAMPLE 5

Preparation of
1-[4-(4-Bromophenoxy)-2-cyano-2-phenylbutyl]-1,2,4-triazole

This compound (5.0 g.) was prepared using the procedures described in Examples 1a, b, c, and d except using 2-(4-bromophenoxy)ethanol in Example 1a and benzyl cyanide in Example 1b, and was obtained as an oil.

EXAMPLE 6

Preparation of
1-[4-(4-Chlorophenoxy)-2-cyano-2-phenylbutyl]-1,2,4-triazole a. Preparation of 2-(4-Chlorophenoxy)ethanol To a flask under a nitrogen atmosphere was added 6.1 g. of lithium aluminum hydride in 60 ml. of dry THF at −4° C. The resulting slurry was stirred and 20.0 g. (0.102 mole) of 4-chlorophenoxyacetic acid in 100 ml. of dry THF was added dropwise. The reaction was stirred overnight and was quenched by cautiously adding saturated aqueous sodium sulfate solution followed by ethyl acetate. The solid was removed by filtration and the aqueous phase was extracted twice with 50 ml. portions of ethyl acetate. The combined ethyl acetate solutions were washed with aqueous saturated sodium chloride solution (brine) and then dried using magnesium sulfate. Removal of the solvent resulted in 17.6 g. (94% yield) of 2-(4-chlorophenoxy)ethanol being isolated as a yellow oil.

b. Preparation of 1-[4-(4-Chlorophenoxy)-2-cyano-2-phenylbutyl]-1,2,4-triazole

This compound (11.0 g.) was prepared using the procedures described in Examples 1a, b, c, and d except using 2-(4-chlorophenoxy)ethanol in Example 1a and benzyl cyanide in Example 1b, and was obtained as an oil.

EXAMPLE 7

Preparation of
1-{2-(4-Chlorophenyl)-2-cyano-5-[4-(N-acetyl-N-methylamino)phenoxy]pentyl}-1,2,4,-triazole a. Preparation of 4-(N-acetyl-N-methylamino)phenyl Acetate.

To a flask was added 20.0 g. of 4-(N-methylamino)phenol, 20 ml. of acetic anhydride, 60 ml. of acetic acid and 10 g. of sodium acetate. The solution was warmed on a steam bath for one hour and water added to clarify the solution. The mixture was allowed to cool, more water added and the resulting solution poured onto solid sodium bicarbonate in an open vessel. The aqueous material was extracted five times with 200 ml. portions of ethyl ether, the ether extracts combined, washed with brine, then dried and concentrated to obtain the crude 4-(N-acetyl-N-methylamino)phenyl acetate which was recrystallized from a mixture of ethyl acetate, hexane and ethanol.

b. Preparation of 4-(N-acetyl-N-methylamino)phenol

The recrystallized 4-(N-acetyl-N-methylamino)phenyl acetate was dissolved in aqueous ethanol and excess aqueous sodium hydroxide added for the hydrolysis. The mixture was stirred two hours, acidified and the resulting solid recovered by filtration to obtain 12.0 g. of 4-(N-acetyl-N-methylamino)phenol.

c. Preparation of 1-Bromo-3-[4-(N-acetyl-N-methylamino)phenoxy]propane

To a flask under a nitrogen atmosphere was added 8.15 g. of 4-(N-acetyl-N-methylamino)phenol in DMF and 10 g. of 1,3-dibromopropane, then 1.3 equivalents of solid potassium t-butoxide in portions while stirring. After reaction, the mixture was allowed to stand overnight, water added, and the solution extracted with diethyl ether. The ether extract was washed successively with aqueous sodium hydroxide, dilute hydrochloric acid, and brine. The washed ether layer was dried, decolorized and concentrated to obtain an oil. The oil was distilled and resulted in isolation of approximately a 1 to 1 mixture of 1-bromo-3-[4-(N-acetyl-N-methylamino)phenoxy]propane and 3-[4-(N-acetyl-N-methylamino)phenoxy]-1-propene.

d. Preparation of 2-(4-Chlorophenyl)-5-[4-(N-acetyl-N-methylamino)phenoxy]pentanenitrile This intermediate (4.6 g.) containing the 3-[4-(N-acetyl-N-methylamino)phenoxy]-1-propene impurity was prepared using the procedure described in Example 1b except using the 1 to 1 mixture of propane and propene prepared in Example 7c.

e. Preparation of 1-{2-(4-Chlorophenyl)-2-cyano-5-[4-(N-acetyl-N-methylamino)phenoxy]pentyl}-1,2,4-triazole To a flask which was cooled by an ice bath was added 20 ml. of water, 30 ml. of chloroform and 10.0 g. of 1-chloromethyl-1,2,4-triazole hydrochloride, then a 50% aqueous solution of sodium hydroxide was added dropwise with stirring until the aqueous layer became basic. The layers were separated, the aqueous layer extracted three times with 25 ml. portions of chloroform, the chloroform layers combined and dried using sodium sulfate. The resulting 1-chloromethyl-1,2,4-triazole was recovered by solvent evaporation.

To a flask was added 0.85 g. of a 50% oil dispersion of sodium hydride. After washing the sodium hydride several times with hexane to remove the oil, a 2 to 1 mixture of toluene and DMF was added to the sodium hydride and the resulting slurry stirred and cooled to 0° C. Then, 4.6 g. of the impure 2-(4-chlorophenyl)-5-[4-(N-acetyl-N-methylamino)phenoxy]pentane nitrile mixture from Example 7d in a solution of DMF and 1.6 g. of 1-chloromethyl-1,2,4-triazole in a solution of DMF were added. The reaction was stirred overnight at room temperature and then poured into ice water. The organic layer was extracted with a mixture of ethyl acetate and ethyl ether, washed with water, dried, filtered and concentrated. The crude product was separated from the olefinic material by column chromatography using ethyl ether and hexane, extracted from the organic layer using aqueous hydrochloric acid, and neutralized with base to obtain the 1-{2-(4-chlorophenyl)-2-cyano-5-[4-(N-acetyl-N-methylamino)phenoxy]pentyl}-1,2,4-triazole as an oil.

The compounds of this invention were tested for fungicidal activity in vivo against cucumber downy mildew (CDM), rice blast (RB), wheat leaf rust (WLR), wheat powdery mildew (WPM), and wheat stem rust (WSR). In tests on cereals (except for rice plants used for testing rice blast), the plants were trimmed about 24 hours prior to the application of the fungicide compound to provide a uniform plant height and to facilitate uniform application of the compound and inoculation with the fungus. The compounds were dissolved in a 2 to 1 to 1 mixture of water, acetone, and methanol, sprayed onto the plants, allowed to dry, and then the plants were inoculated with the fungus 24 hours after spraying. Each test utilized control plants which were sprayed with the water, acetone, and methanol mixture and inoculated with the fungus. The remainder of the technique for each of the tests is given below. Results are reported as percent disease control (percentage of a plant treated with a compound of the present invention lacking disease signs or symptoms compared to an inoculated, untreated control plant).

Cucumber Downy Mildew (CDM):

*Pseudoperonospora cubensis* was maintained on leaves of live Marketer cucumber plants in a constant temperature room at 65°–75° F. in humid air with moderate light intensity for 7 to 8 days. A water suspension of the spores from infested leaves was obtained and the spore concentration was adjusted to about 100,000 per ml of water. Marketeer cucumber seedlings previously treated with compounds of this invention were inoculated with the spore concentration by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65°–75° F. Seven days after inoculation, the percent disease control was determined.

Rice Blast (RB):

M201 rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75°–85° F.) for about 24 hours, then placed in a greenhouse environment (70°–75° F.). Seven to eight days after inoculation, the percent disease control was determined.

Wheat Leaf Rust (WLR):

*Puccinia recondita* (f. sp. *tritici* Races PKB and PLD) was cultured on seven day old wheat (cultivar Fielder) over a 14 day period in the greenhouse. Spores were collected from the leaves, cleaned by sieving through a 250 micron opening screen and stored or used fresh. A spore suspension was prepared from dry uredia by adding 20 mg (9.5 million) per ml of Soltrol oil. The suspension was dispensed into gelatin capsules (0.7 ml capacity) which attach to the oil atomizers. One capsule was used to inoculate a flat of twenty of the two inch square pots of seven day old Fielder wheat. The plants were placed in a darkmist chamber (18°–20° C. and 100% relative humidity) for 24 hours. The plants were then put in the greenhouse for the latent period and scored after 10 days for disease levels. Protective and curative tests were inoculated one day after and two days, respectively, before spraying the plants with the test chemicals.

Wheat Powdery Mildew (WPM):

*Erysiphe graminis* (f. sp. *tritici*) was cultured on Hart wheat seedlings in a controlled temperature room at 65°–75° F. Mildew spores were shaken from the culture plants onto Hart wheat seedlings which had been sprayed previously with the fungicide compound. The inoculated seedlings were kept in a controlled temperature room at 65°–75° F. and subirrigated. The percent disease control was rated eight days after the inoculation.

Wheat Stem Rust (WSR):

*Puccinia graminis* (f. sp. *tritici* Race 15B-2) was cultured on Tyler wheat seedlings for a period of 14 days in a greenhouse. The remainder of the test protocol was conducted as previously described for wheat leaf rust. Table 3 lists fungicidal data for Examples 1–7 of the present invention.

TABLE 3

| | Fungicide Test Results[1] | | | | |
|---|---|---|---|---|---|
| Ex. No. | CDM | RB | WLR | WPM | WSR |
| 1 | 50/450 | 87/450 | —/—[2] | 82/450 | 100/450 |
| 2 | 0/450 | 20/450 | —/— | 97/450 | 98/450 |
| 3 | 0/450 | 35/450 | —/— | 98/450 | 78/450 |
| 4 | 0/450 | 0/450 | —/— | 70/450 | 78/450 |
| 5 | 0/300 | 0/300 | —/— | 100/300 | 100/300 |
| 6 | 20/300 | 40/300 | —/— | 60/300 | 90/300 |
| 7 | 0/300 | 0/300 | 95/300 | 95/300 | —/— |

[1]Values Given as (% Control)/(Grams/Hectare) Application Rate.
[2]Not Tested.

The 1,2,4-triazoles, and the enantiomorphs, acid addition salts and metal salt complexes thereof are useful as agricultural fungicides and as such can be applied to various loci such as the seed, the soil or the foliage. These compounds as a class show broad spectrum antifungal activity when applied to cereal grains such as wheat, barley, rye and rice, peanuts, beans, grapes, turf, fruit orchards, vegetables and golf courses. The compounds of this invention are especially strong against powdery mildews, rusts, and Helminthosporium diseases in cereal crops such as wheat, barley, rye, or rice. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, suspension concentrates, aerosols, or flowable emulsion concentrates. In such formulations, the compounds are extended with a liquid or solid carrier and, when desired, suitable surfactants are incorporated. It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers, Annual".

In general, the compounds of this invention can be dissolved in certain solvents such as acetone, methanol, ethanol, DMF, pyridine or DMSO and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90%, and in flowable emulsion concentrates, can be as high as about 75%.

Wettable powders, suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 5% to about 98%, preferably from about 25% to about 75%. A typical wettable powder is made by blending 50 parts of a 1,2,4-triazole, 45 parts of a synthetic precipitated hydrated silicon dioxide sold under the trademark Hi-Sil®, and 5 parts of sodium lignosulfonate. In another preparation a kaolin type (Barden) clay is used in place of the Hi-Sil in the above wettable powder, and in another such preparation 25% of the Hi-Sil® is replaced with a synthetic sodium silico aluminate sold under the trademark Zeolex® 7.

Dusts are prepared by mixing the 1,2,4-triazoles, or the enantiomorphs, geometric isomers, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to a range of about 1% to about 10% use concentration.

The 1,2,4-triazoles, and the enantiomorphs, geometric isomers, salts and complexes thereof can be applied as fungicidal sprays by methods commonly employed, such as conventional high gallonage hydraulic sprays, low gallonage sprays, air blast sprays, aerial sprays and dusts. The dilution and rate of application will depend upon the type of equipment employed, the method of application and diseases to be controlled, but the preferred effective amount is usually from about 0.05 pound to about 5.0 pounds per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.05 to about 5.0 pounds per acre. As a foliar fungicide, the toxicant is usually applied to growing plants at a rate of from about 0.25 to about 1.0 pound per acre.

Fungicides which can be combined with the fungicides of this invention include:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, α-[2-(4-chlorophenyl)ethyl]-α-phenyl-1H-1,2,4-triazole-1-propanenitrile, hexaconazole, cyprconazole, tebuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl- 5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as: chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

We claim:

1. A compound of the formula

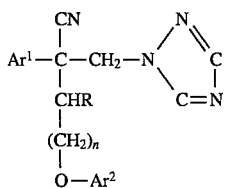

wherein

Ar¹ and Ar² are each independently phenyl or napthyl unsubstituted or substituted with one or two substituents each independently selected from the group consisting of halogen, $(C_1-C_4)$alkyl, halo $(C_1-C_4)$ alkyl, $(C_1-C_2)$alkoxy, halo$(C_1-C_4)$alkoxy, N-alkyl-N-(alkylcarbonyl)amino;

n is and integer from one to about four;

R is hydrogen or methyl; or the agronomically acceptable enantiomorph, acid addition salts or metal salt complexes thereof.

2. The compound of claim 1 wherein

Ar¹ and Ar² are each independently phenyl or phenyl substituted with one or two substituents each independently selected from the group consisting of halogen, $(C_1-C_2)$alkyl, halo$(C_1-C_2)$alkyl, $(C_1-C_2)$alkoxy, halo$(C_1-C_2)$alkoxy and N-acetyl-N-methylamino, and R is hydrogen.

3. The compound of claim 2 wherein Ar¹ and Ar² are each independently selected from the group consisting of phenyl, phenyl substituted with one or two halogens selected from fluoro, chloro and bromo, and 4-(N-acetyl-N-methylamino)phenyl.

4. The compound of claim 3 wherein Ar¹ is phenyl, 4-chlorophenyl, 4-fluorophenyl, 2,4-dichlorophenyl or 2,4-difluorophenyl and Ar² is phenyl, 4-chlorophenyl, 4-fluorophenyl, 2,4-dichlorophenyl, 2,4-difluorophenyl, 4-bromophenyl or 4-(N-acetyl-N-methylamino)phenyl.

5. The compound of claim 4 wherein Ar¹ is 4-chlorophenyl, Ar² is phenyl and n is one.

6. The compound of claim 4 wherein Ar¹ is phenyl, Ar² is 4-bromophenyl and n is one.

7. A fungicidal composition for controlling phytopathogenic fungi which comprises an agronomically acceptable carrier and a fungicidally effective amount of the compound of claim 1.

8. A fungicidal composition for controlling phytopathogenic fungi which comprises an agronomically acceptable carrier and a fungicidally effective amount of the compound of claim 3.

9. A fungicidal composition for controlling phytopathogenic fungi which comprises an agronomically acceptable carrier and a fungicidally effective amount of the compound of claim 5.

10. A fungicidal composition for controlling phytopathogenic fungi which comprises an agronomically acceptable carrier and a fungicidally effective amount of the compound of claim 6.

11. A method for controlling phytopathogenic fungi which comprises applying to the locus where control is desired a fungicidally effective amount of the compound of claim 1.

12. A method for controlling phytopathogenic fungi which comprises applying to the locus where control is desired a fungicidally effective amount of the compound of claim 3.

13. A method for controlling phytopathogenic fungi which comprises applying to the locus where control is desired a fungicidally effective amount of the compound of claim 5.

14. A method for controlling phytopathogenic fungi which comprises applying to the locus where control is desired a fungicidally effective amount of the compound of claim 6.

* * * * *